United States Patent
Murphy et al.

(10) Patent No.: US 10,024,826 B2
(45) Date of Patent: Jul. 17, 2018

(54) ANALYSIS OF DRIED BLOOD SPOT SAMPLES IN A MICROFLUIDIC SYSTEM WITH DILUTION OF EXTRACTED SAMPLES

(75) Inventors: James P. Murphy, Franklin, MA (US); Michael J. Tomany, Thompson, CT (US); Joseph D. Michienzi, Plainville, MA (US); Paul Rainville, Princeton, MA (US); Robert S. Plumb, Milford, MA (US); Geoff C. Gerhardt, Millbury, MA (US); Moon Chul Jung, Arlington, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 470 days.

(21) Appl. No.: 14/238,653

(22) PCT Filed: Aug. 22, 2012

(86) PCT No.: PCT/US2012/051892
§ 371 (c)(1),
(2), (4) Date: Feb. 12, 2014

(87) PCT Pub. No.: WO2013/028774
PCT Pub. Date: Feb. 28, 2013

(65) Prior Publication Data
US 2014/0208836 A1    Jul. 31, 2014

Related U.S. Application Data

(60) Provisional application No. 61/525,963, filed on Aug. 22, 2011, provisional application No. 61/525,970, filed on Aug. 22, 2011.

(51) Int. Cl.
*G01N 30/06* (2006.01)
*G01N 30/16* (2006.01)
(Continued)

(52) U.S. Cl.
CPC ........ *G01N 30/06* (2013.01); *B01L 3/502715* (2013.01); *G01N 30/16* (2013.01);
(Continued)

(58) Field of Classification Search
CPC ........ G01N 30/06; G01N 30/16; G01N 30/88; G01N 33/49; B01L 2300/0816; B01L 2300/0874
(Continued)

(56) References Cited

U.S. PATENT DOCUMENTS

| 5,500,071 A | 3/1996 | Kaltenbach et al. |
| 5,571,410 A | 11/1996 | Swedberg et al. |

(Continued)

FOREIGN PATENT DOCUMENTS

| EP | 2330402 A1 | 6/2011 |
| JP | 2002524755 A | 8/2002 |

(Continued)

OTHER PUBLICATIONS

International Preliminary Report on Patentability in counterpart international patent application No. PCT/US12/51892, dated Mar. 6, 2014; 7 pages.

(Continued)

*Primary Examiner* — John Fitzgerald
*Assistant Examiner* — Rodney T Frank
(74) *Attorney, Agent, or Firm* — Schmeiser, Olsen & Watts LLP

(57) ABSTRACT

An apparatus for use in a chromatography system includes a microfluidic substrate having a fluidic channel configured as an analytical chromatographic column and a fluidic port on one side of the microfluidic substrate. The fluidic port opens at a head end of the analytical chromatographic column. A dried blood spot (DBS) collection device holds one or more dried biological samples. The DBS collection (Continued)

device is directly coupled to the microfluidic substrate whereby one of the biological samples is placed into fluidic communication with the fluidic channel of the microfluidic substrate and an extraction of that biological sample flows toward the head end of the analytical chromatographic column. A diluent source fluidically coupled to the fluidic port supplies a solvent to the head end of the analytical column to dilute the extracted biological sample before the biological sample flows into the analytical chromatographic column.

24 Claims, 8 Drawing Sheets

(51) Int. Cl.
*B01L 3/00* (2006.01)
*G01N 30/88* (2006.01)
*G01N 33/49* (2006.01)
G01N 30/60 (2006.01)
G01N 30/00 (2006.01)
G01N 1/38 (2006.01)

(52) U.S. Cl.
CPC ............ *G01N 30/88* (2013.01); *G01N 33/49* (2013.01); *B01L 2300/0816* (2013.01); *B01L 2300/0874* (2013.01); *B01L 2300/0887* (2013.01); *B01L 2300/1827* (2013.01); *G01N 30/6095* (2013.01); *G01N 2001/383* (2013.01); *G01N 2030/009* (2013.01); *G01N 2030/062* (2013.01)

(58) Field of Classification Search
USPC ........................................ 73/61.55
See application file for complete search history.

(56) References Cited

U.S. PATENT DOCUMENTS

| | | | |
|---|---|---|---|
| 5,658,413 A | 8/1997 | Kaltenbach et al. | |
| 5,997,708 A | 12/1999 | Craig | |
| 6,240,790 B1 | 6/2001 | Swedberg et al. | |
| 6,303,389 B1 | 10/2001 | Levin et al. | |
| 6,632,399 B1 | 10/2003 | Kellogg et al. | |
| 7,028,536 B2 | 4/2006 | Karp et al. | |
| 7,261,812 B1 | 8/2007 | Karp et al. | |
| 7,811,452 B2 | 10/2010 | Yin et al. | |
| 7,955,863 B2 | 6/2011 | Cox | |
| 8,304,230 B2 | 11/2012 | Toner et al. | |
| 8,753,868 B2 | 6/2014 | Duthie et al. | |
| 8,940,147 B1 | 1/2015 | Bartsch et al. | |
| 2002/0155032 A1 | 10/2002 | Liu et al. | |
| 2005/0037484 A1 | 2/2005 | Staimer et al. | |
| 2010/0171055 A1 | 7/2010 | Dourdeville | |
| 2010/0199750 A1* | 8/2010 | Arnold .............. | B01L 3/502715 73/61.56 |
| 2010/0210008 A1 | 8/2010 | Strand et al. | |
| 2010/0213063 A1 | 8/2010 | Lenhausem et al. | |
| 2011/0053289 A1 | 3/2011 | Lowe et al. | |
| 2011/0107822 A1 | 5/2011 | Bunner et al. | |
| 2011/0129940 A1 | 6/2011 | Gijlers et al. | |
| 2011/0133077 A1 | 6/2011 | Henion et al. | |
| 2012/0028342 A1 | 2/2012 | Ismagilov et al. | |
| 2013/0116597 A1 | 5/2013 | Rudge et al. | |
| 2013/0164856 A1* | 6/2013 | Jebrail .............. | B01L 3/502792 436/86 |

FOREIGN PATENT DOCUMENTS

| | | | |
|---|---|---|---|
| JP | 2004144568 A | 5/2004 |
| JP | 2005083510 A | 3/2005 |
| JP | 2005509142 A | 4/2005 |
| JP | 2010511154 A | 4/2010 |
| JP | 2011506922 A | 3/2011 |
| WO | 2004101151 A1 | 11/2004 |
| WO | 2006123578 A1 | 11/2006 |
| WO | 2010111265 A1 | 9/2010 |
| WO | 2010138667 A1 | 12/2010 |
| WO | 2011044350 A2 | 4/2011 |
| WO | 2013067520 A1 | 5/2013 |

OTHER PUBLICATIONS

Extended European Search Report in counterpart European Patent Application No. 12826104.7, dated May 11, 2015; 6 pages.
Heinig, Kataja, et al., "Sensitive determination of a drug candidate in dried blood spots ysing a TLC-MS interface integrated into a column-switching LC-MS/MS system", Bioanalysis, Future Science, Nov. 2010, pp. 1873-1882, vol. 2.
Abu-Rabie, Paul and Neil Spooner, "Direct Quantitative Bioanalysis of Drugs in Dried Blood Spot Samples Using a Thin-Layer Chromatography Mass Spectrometer Interface", Analytical Chemistry, Dec. 15, 2009, pp. 10275-10284, vol. 81, No. 24.
Miller, John H., et al., "Direct analysis of dried blood spots by in-line desorption combined with high-resolution chromatography and mass spectrometry for quantification of maple syrup urine disease biomarkers leucine and isoleucine", Analytical and Bioanalytical Chemistry, Feb. 18, 2011, pp. 237-244, vol. 400.
International Search Report & Written Opinion in related international patent application No. PCT/US12/51892, dated Nov. 2, 2012; 8 pages.
Notice of Rejection in counterpart Japanse Patent Application No. 2014-527268, dated May 24, 2016; 5 pages.
Extended European Search Report in related European Patent Application No. 12825812.6, dated Mar. 24, 2015; 7 pages.
International Preliminary Report on Patentability in related international patent application No. PCT/US12/51876, dated Mar. 6, 2014; 7 pages.
International Search Report & Written Opinion in related international patent application No. PCT/US12/51876, dated Nov. 5, 2012; 8 pages.
Non-Final Office Action in related U.S. Appl. No. 14/238,038, dated Apr. 19, 2016; 12 pages.
Notice of Rejection in related Japanse Patent Application No. 2014-527264, dated Jul. 5, 2016; 10 pages.
Final Office Action in related U.S. Appl. No. 14/238,038, dated Oct. 20, 2016; 14 pages.
Notice of Allowance in related U.S. Appl. No. 14/238,038, dated Mar. 13, 2017; 7 pages.

* cited by examiner

ANALYSIS OF DRIED BLOOD SPOT SAMPLES IN A MICROFLUIDIC SYSTEM WITH DILUTION OF EXTRACTED SAMPLES

RELATED APPLICATIONS

This application claims priority to and the benefit of the filing date of U.S. Provisional Application Ser. No. 61/525,963, filed Aug. 22, 2011, titled "Microfluidic Device with DBS Card Interface," and of U.S. Provisional Application Ser. No. 61/525,970, filed Aug. 22, 2011, titled "Analysis of Dried Blood Spot Samples in a Microfluidic System with Dilution of Extracted Samples," the entireties of which applications are incorporated by reference herein.

FIELD OF THE INVENTION

The invention relates generally to chromatography. More specifically, the invention relates to systems and methods for extracting, diluting, and analyzing dried blood spot samples.

BACKGROUND

Chromatography is a set of techniques for separating a mixture into its constituents. Well-established separation technologies include HPLC (High Performance Liquid Chromatography), UPLC (Ultra Performance Liquid Chromatography), and SFC (Supercritical Fluid Chromatography). HPLC systems use high pressure, ranging traditionally between 1,000 psi (pounds per square inch) to approximately 6,000 psi, to generate the flow required for liquid chromatography in packed columns. In contrast to HPLC, UPLC systems use columns with smaller particulate matter and higher pressures approaching 20,000 psi to deliver the mobile phase. SFC systems use highly compressible mobile phases, which typically employ carbon dioxide ($CO_2$) as a principle component.

In general, in a liquid chromatography (LC) application, a solvent delivery system takes in and delivers a mixture of liquid solvents to an autosampler (also called an injection system or sample manager), where an injected sample awaits the arrival of this mobile phase. The mobile phase carries the sample through an analytical column (also referred to as a separation column). In the column, the mixture of the sample and mobile phase divides into bands depending upon the interaction of the mixture with the stationary phase in the column. A detector, for example, identifies and quantifies these bands as they exit the column.

Proteomic analyses often utilize a trap column for sample enrichment and cleaning prior to separation of the sample in an analytical column. Often, different packing material chemistries are used for the trap and analytical columns; sample components trapped on the trap column may be serially driven from the trap to the analytical column during a gradient-based mobile phase elution process. The components can be initially focused at the head of the analytical column, because of the different chemistry, until the gradient attains a level that drives the sample components from the chemistry of the analytical column. In addition, some chromatography instruments use a microfluidic substrate. Such substrates can ease the handling of small samples and reduce undesirable effects, such as dispersion.

SUMMARY

In one aspect, the invention features a chromatography apparatus comprising a microfluidic substrate having a fluidic channel configured as an analytical chromatographic column and a fluidic port on one side of the microfluidic substrate. The fluidic port opens at a head end of the analytical chromatographic column. A dried blood spot (DBS) collection device holds one or more dried biological samples. The DBS collection device is directly coupled to the microfluidic substrate, whereby one of the biological samples is placed into fluidic communication with the fluidic channel of the microfluidic substrate and an extraction of that biological sample flows toward the head end of the analytical chromatographic column A diluent source is fluidically coupled to the fluidic port. The diluent source supplies a solvent to the head end of the analytical column to dilute the extracted biological sample before the biological sample flows into the analytical chromatographic column.

In another aspect, the invention features a method of separating a biological sample into constituent components. The method comprises coupling a dried blood spot (DBS) collection device, holding at least one dried biological sample, directly to a microfluidic substrate, extracting an analyte from the dried biological sample and passing the extracted biological sample into a fluidic channel of the microfluidic substrate, diluting the extracted biological sample in the fluidic channel before the extracted biological sample reaches an analytical chromatographic column, and separating, by the analytical chromatographic column, the diluted biological sample into constituent components.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Liquid chromatography (LC) systems described herein, such as HPLC, UPLC, and SFC systems, are configured to directly analyze an analyte extracted from a dried biological sample, referred to as a dried blood spot (DBS), using reverse phase chromatography. In a reverse phase separation, samples are preferably constituted with an aqueous solvent. This allows the sample to be properly focused at the head of a column. Samples, however, may consist of varied amounts of organic solvent. An extracted blood spot sample, for example, may consist of as much as 90% organic solvent. When the composition of organic solvent is too high, the analyte may not be properly retained on a reverse phase column. At-head-of-the-column dilution for DBS analyses assists in focusing the analyte on the head of a reversed phase column.

To extract the analyte from the DBS in on-line fashion, such LC systems employ an apparatus adapted to couple a dried blood spot directly onto a microfluidic substrate. The microfluidic substrate has a fluidic channel configured as an analytical column A fluidic port opens into a head end of the analytical column A dried blood spot (DBS) collection device, fluidically coupled to the fluidic channel of the microfluidic substrate, holds one or more dried biological samples. A reconstituted biological sample, extracted from the dried blood spot, flows towards the head end of the analytical chromatographic column Before the biological sample flows into the analytical column, a diluent pump supplies a solvent to the head end of the analytical column through the fluidic port of the microfluidic substrate to dilute the extracted biological sample. Integrated on the same microfluidic substrate as the analytical column, or formed in a separate microfluidic substrate, a trapping/enhancement column lies in a fluidic path between the dried blood spot and the analytical column, and operates to prepare the extracted biological sample for analysis.

A cartridge assembly can house any of the various embodiments of multi-tile microfluidic devices described herein, to provide an interface for the microfluidic devices to an analytical apparatus or mass spectroscopy (MS) unit, for example, an ACQUITY® or TRIZAIC® LC/MS system (available from Waters Corporation, Milford, Mass.).

Figure 1:
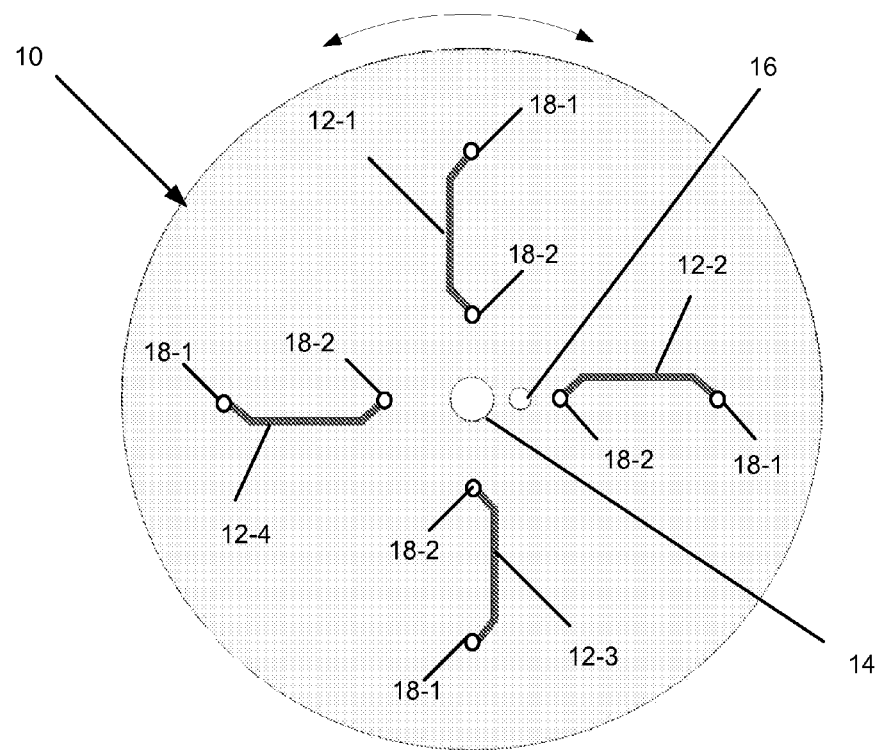
FIG. 1 is a diagram of an embodiment of a disc-shaped microfluidic substrate having formed therein a plurality of channels arranged to accommodate rotary indexing from channel to channel.

FIG. 1 shows an embodiment of a disc-shaped microfluidic substrate 10 having plurality of identical handlebar-shaped microfluidic channels 12-1, 12-2, 12-3, and 12-4 (generally, 12) arranged radially about a central opening 14, like the four cardinal points of a compass. Adjacent to the center hole 14 is a smaller hole 16, used to mark a particular channel (here, for example, channel 12-1). A marked channel enables tracking of the current indexing position of the channels 12 (i.e., the current location of the hole 16 can be used as a reference point for identifying which channels have already been used). One end of each channel 12 has an ingress fluidic port 18-1 disposed on one side of the tile 10, and the opposite end of each channel 12 has an egress fluidic port 18-2 disposed on the other (opposite) side of the tile 10. The egress fluidic port 18-2 may be through-hole, opening to both sides of the microfluidic substrate 10, for facilitating waste removal and at head column dilution, as described in more detail below. In one embodiment, the thickness of the microfluidic substrate 10 can range from approximately 750 μm to greater than 1 mm, and its diameter can range between approximately 1 and 3 inches. The length of the channels can range between approximately 5 cm and 20 cm long; their inner diameters (IDs) can range between approximately 150 μm to 300 μm (preferably 300 μm).

The microfluidic substrate 10 preferably has a multilayer ceramic-based construction. Each microfluidic channel 12 can pass through one or more of the layers (i.e., the depth of a given channel 12 can extend through multiple layers). In addition, different channels 12 can be formed on different layers (with intervening blank layers) of the microfluidic substrate 10, thus allowing for a 3-dimensional (3D) non-interfering overlap of channels. This 3D stacking of channels can contribute to the compactness of the microfluidic substrate 10.

The microfluidic substrate 10 is adapted to rotate about a central axis passing through the center of the center hole 14 (perpendicular to the plane of the figure). The angles between each pair of adjacent channels 12 are the same. For example, for a microfluidic substrate 10 having four identical channels 12, the angle between each pair of adjacent channels is 90 degrees. The angle for a microfluidic substrate with five identical channels, for example, is 72 degrees.

The microfluidic channels 12 can preferably be used as trapping/enhancement columns. When the performance of a channel 12 currently in use has declined below a satisfactory level, for example, the microfluidic substrate 10 can be indexed (i.e., rotated by one position) to disengage the currently used channel 12 and to bring an adjacent channel 12 into use. Such rotation can be manual or automated.

Figure 2:
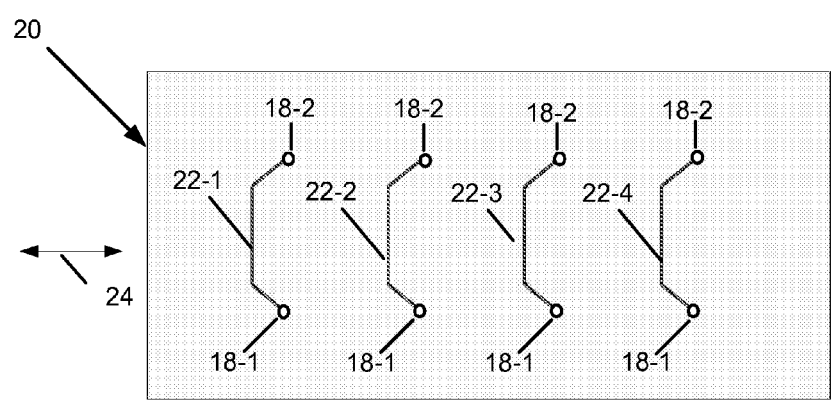
FIG. 2 is a diagram of an embodiment of a card-shaped microfluidic substrate having formed therein a plurality of channels arranged to accommodate linear indexing from channel to channel.

FIG. 2 shows another embodiment of a microfluidic substrate 20 with plurality of identical microfluidic channels 22-1, 22-2, 22-3, and 22-4 (generally, 22) arranged in a row. In one embodiment, the microfluidic substrate 20 is approximately 750 μm to greater than 1 mm in thickness, approximately 3 inches in length, approximately 1 or more inches in width, and the channels 22 have a diameter ranging between approximately 150 μm to 300 μm (preferably 300 μm) and a length ranging between approximately 5 cm and 20 cm.

Similar to the embodiment of FIG. 1, the microfluidic channels 22 can preferably be used as trapping/enhancement columns. For this embodiment, indexing of the microfluidic substrate 20 to change from using one channel 22 to a neighboring channel 22 in the row occurs in a linear direction along the direction signified by the arrow 24. Such linear indexing can be manual or automated.

Figure 3:
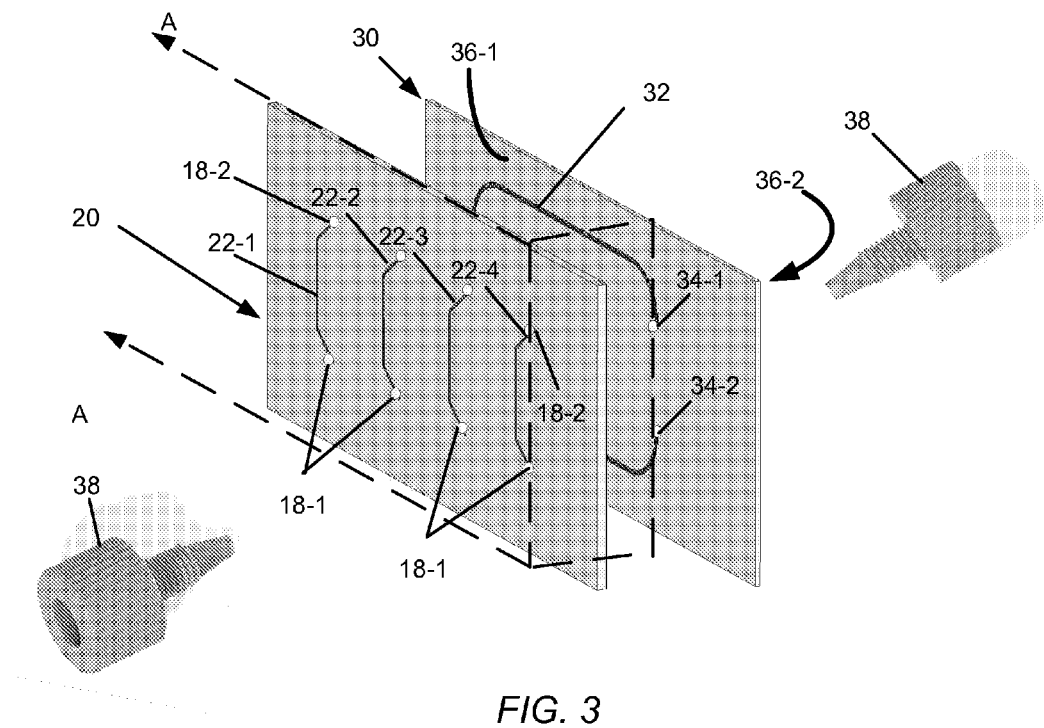
FIG. 3 is a diagram of an embodiment of a first microfluidic substrate, having multiple trapping/enhancement columns, arranged in-line with a second microfluidic substrate, having an analytical column.

FIG. 3 shows a microfluidic device comprised of a first substantially rigid and planar microfluidic substrate 20 of the kind described in FIG. 2, having multiple trapping/enhancement columns 22, arranged in-line with a second substantially rigid and planar microfluidic substrate 30, having, for example, an analytical column 32. In this arrangement, the trapping/enhancement columns 22 and analytical column 32 are on two separate microfluidic substrates. The separate substrates for the trapping/enhancement and analytical columns can be used, for example, for thermal isolation and/or pre-loading of samples. Alternatively, the column 32 on the second microfluidic substrate 30 can be an infusion column.

The analytical column 32 has a fluidic port 34-1 on the inside-facing side 36-1 of the substrate 30 and another fluidic port (in phantom) opening on an outside-facing side 36-2. In this example, the analytical column 32 is an open loop, starting and terminating at the fluidic ports 34-1, 34-2. This shape of the analytical column 32 is just one example. Other embodiments of the analytical column 32 can have a fluidic port that opens at an edge of the substrate 30, instead of opening on the opposite side 36-2. In one embodiment, the analytical column 32 preferably has a 150 μm inner diameter (ID. The diameter of the column 32 preferably ranges between approximately 75 μm and 300 μm (a diameter size of 300 μm may provide increased sensitivity for small molecule and biopharmaceutical analyses in comparison to traditionally larger diameter formats), and the length of the column 32 preferably ranges between 5 cm and 20 cm.

Preferably, the substrates 20, 30 abut each other, back-to-back, with the egress (inside-facing) port 18-2 of the first microfluidic substrate 20 aligning with the fluidic port 34-1 on the inside-facing side 36-1 of the second microfluidic substrate 30. In one embodiment, fluidic nozzles 38 connect to opposite sides of the combined microfluidic device assembly, specifically, to the ingress port 18-1 of the first microfluidic substrate 20 and to the rear-facing port 34-2 of the second microfluidic substrate 30. Tubing (for example, fused silica, stainless steel) connects to these fluidic nozzles 38 for the delivery or extraction of fluid.

Figure 4:
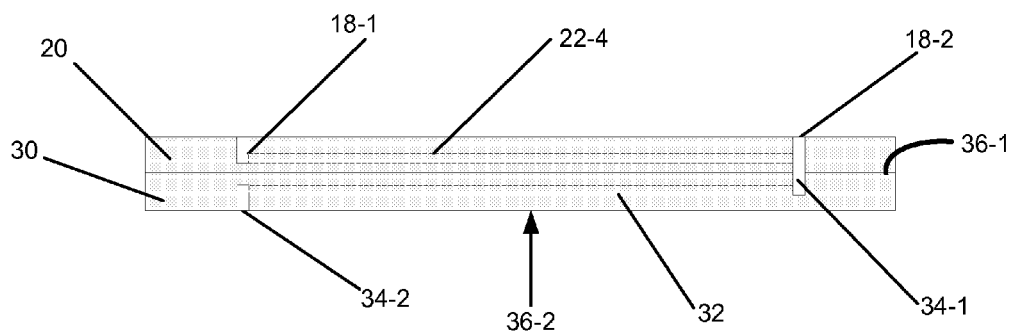
FIG. 4 is a cross-section, taken generally along the line AA in FIG. 3, of the first microfluidic substrate abutting the second microfluidic substrate to provide a fluidic path therebetween.

FIG. 4 shows a cross-section (taken generally along a line like AA in FIG. 3) of the first microfluidic substrate 20 abutting the second microfluidic substrate 30. The cross-section passes through the ports 18-1, 18-2, 34-1, 34-2 of the substrates 20, 30. The egress fluidic port 18-2 of the first microfluidic substrate 20 aligns and makes a fluidic connection with the inside-facing fluidic port 34-1 of the second microfluidic substrate 30.

To accommodate the high fluidic pressures of some chromatography systems in which the microfluidic device may be deployed, without leakage, a variety of features can be implemented. Mechanical fittings (not shown) with a coupling component can be used to hold the substrates 20, 30 together. Fluidic couplers can join aligned fluidic ports of the two microfluidic substrates. Such couplers can have a lumen or channel for passing fluid from the trap tile 20 to the analytical tile 30. Alignment markers, guides, or other such features can facilitate alignment between the substrates 20, 30 to achieve a precise alignment between the ports 18-2, 34-1. Polyimide gaskets can surround the fluidic ports 18, 34 and facilitate sealing between those ports brought into intimate contact. In addition, a microfluidic cartridge assembly used to house the microfluidic device (and interface the device to an analytical apparatus) can have features that guide the alignment and urge the substrates 20, 30 together. Further, a clamping mechanism can apply a mechanical force to one side of the microfluidic cartridge assembly that houses the microfluidic device, urging the substrates together against a "hard stop".

Figure 5:
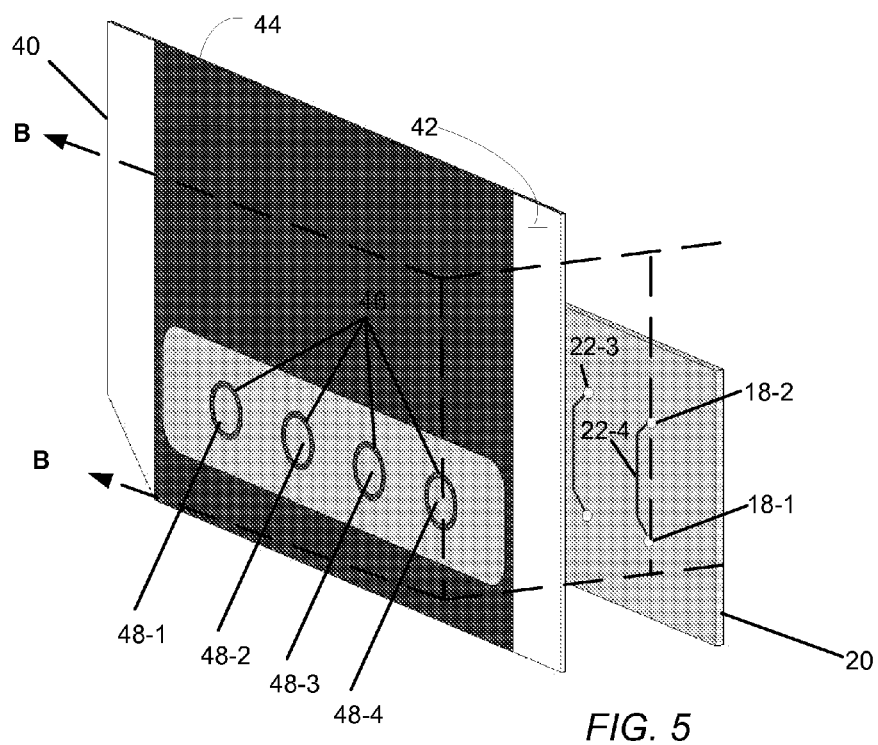
FIG. 5 is a diagram of an embodiment of a collection device, referred to as a DBS (dried blood spot) card, aligned for coupling to a first microfluidic substrate having multiple trapping/enhancement columns.

FIG. 5 shows an embodiment of a planar collection device 40 aligned for coupling to a first microfluidic substrate 20 of the kind shown in FIG. 2 having multiple trapping/enhancement columns 22 (of which columns 22-3 and 22-4 are visible). The planar collection device 40 may be referred to as a DBS (dried blood spot) card 40 without any implicit limitation to the types of biological fluids with which the DBS card 40 may be used. The DBS card 40 includes a collection substrate 42 comprised of filter paper or other material capable of absorbing a biological fluid (e.g., blood).

A pattern 44 may be printed into the collection substrate 42 using an ink or other printable substance. In this embodiment, the pattern 44 has a rectangular shape with four circular openings 46. The printable substance fills pores in the filter paper and prevents fluids from being absorbed in the region with the impermeable pattern 44. In some embodiments, a hydrophobic ink is used to produce a pattern 44 that is impermeable to aqueous biological fluids. Examples of the ink or printable substance include, but are not limited to, a wax, a photoresist, a sol-gel precursor, or a polymer precursor. The portions of the collection substrate 42 that are not printed (i.e., the four circular openings 46 in the pattern) are collection regions 48-1, 48-2, 48-3, and 48-4 (generally, 48) for receiving biological fluid samples. The collection regions 48 may be referred to as dried blood spots 48 without any implicit limitation to the types of biological fluids deposited on the spots 48.

In other embodiments, the planar collection device 40 has a paper-based substrate 42 with the impermeable pattern 44 and a number of sample collection regions 48 that function as storage wells. The impermeable pattern 44 is formed in the substrate 42 and can be configured to precisely define the collection volumes, that is, the fluid volume capacities of the sample collection regions 48. In various other embodiments, patterns can include multiple inlet regions or fluidic paths that guide fluid samples to one or more lateral flow filters or other regions of the device. In still another embodiment, the planar collection substrate 42 is a porous thermoplastic material that is heated in one or more defined spatial regions. The heated regions are converted into non-porous and impermeable regions by deformation or melting. The impermeable regions may retain a minor porosity; however, the remaining porosity is insufficient to permit significant infiltration of a fluid sample. This embodiment dispenses with the need to print with an impermeable ink or to apply a non-porous material to the substrate.

The DBS card 40 is aligned with the microfluidic substrate 20 such that at least one of the dried blood spots 48 aligns with an ingress port 18 of one of the trapping/enhancement columns 22. For example, in FIG. 5, the dried blood spot 48-4 is aligned with the ingress port 18-1 of the trapping/enhancement column 22-4. In one embodiment, each dried blood spot 48 aligns with an ingress port 18 of a different one of the trapping/enhancement columns 22. Depending upon the desired application, the multiple trapping/enhancement columns 22 can contain a different resin.

Figure 6:
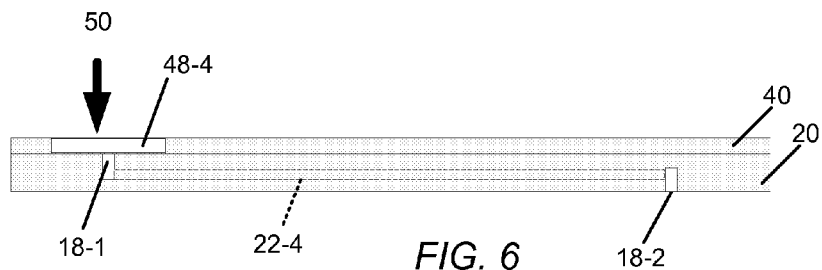
FIG. 6 is a cross-section, taken generally along the line BB in FIG. 5, of the DBS card abutting the first microfluidic substrate to provide a fluidic path for a biological fluid sample extracted from the DBS card.

FIG. 6 shows a cross-section (taken generally along a line like BB in FIG. 5) of the DBS card 40 abutting the microfluidic substrate 20. The cross-section passes through the ports 18-1, 18-2 of the fluidic channel 22-4 in the microfluidic substrate 20 and through the dried blood spot 48-4. Instead of using a complete DBS card 40, dried blood spots 48 can be individually punched out and coupled directly to the microfluidic substrate 20 at the ingress fluidic port 18-1. The extraction principles as applied to the DBS card 40 apply also to individual dried blood spots. During extraction of a biological fluid sample held on the dried blood spot 48-4, the fluid sample is reconstituted by passing an extraction fluid or solvent in the direction of the dashed arrow 50 through the dried sample spot 48-4. In some embodiments, the extraction fluid or solvent is an organic solvent or an aqueous solvent. In another embodiment, the extraction solvent is a supercritical solvent used in a SFC system, for example, supercritical carbon dioxide.

Figure 7:
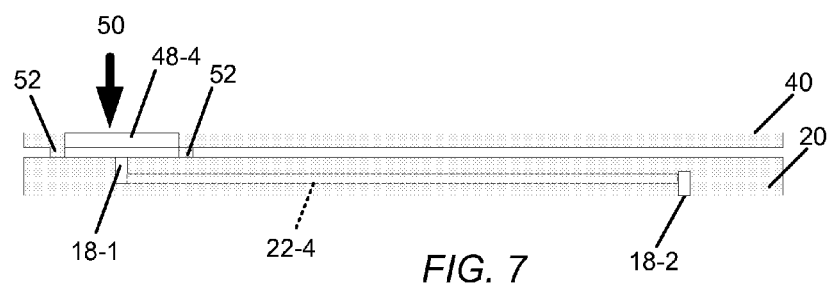
FIG. 7 is another cross-section, taken generally along the line BB in FIG. 5, of the DBS card coupled to the first microfluidic substrate with an intervening leak-proof seal, which provides a fluidic path for a biological fluid sample extracted from the DBS card.

The extracted biological sample flows through the opposite side of the dried sample spot 48-4 into the fluidic port 18-1 of the microfluidic substrate 20 and into the trapping/enhancement column 22-4. A feature of the DBS card 40 can provide a leak-proof seal (e.g., reference numeral 52 of FIG. 7) around the dried blood spot 48-4 that ensures the full volume of reconstituted sample flows into the ingress fluidic port 18-1 of the microfluidic substrate 20. Different mechanisms can be used for extracting the analyte from the dried blood spot without departing from the principles described herein. For example, instead of passing the extraction solvent through the dried blood spot, an extraction device can pass the extraction solvent over the top of the dried blood spot and recover the analyte from the top of the dried blood spot before directing the extracted biological sample into the ingress fluidic port 18-1 of the microfluidic substrate 20.

Figure 8:
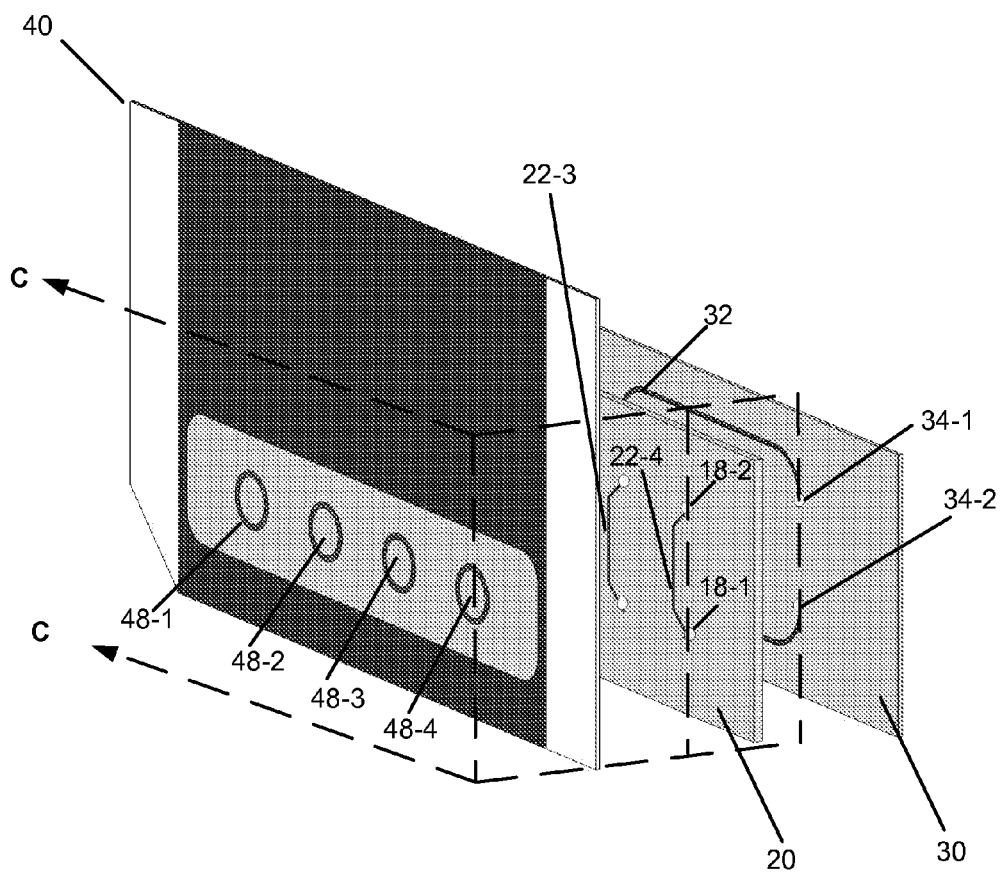
FIG. 8 is a diagram of an embodiment of a DBS card aligned for coupling to a first microfluidic substrate, having multiple trapping columns, arranged in-line with a second microfluidic substrate having, for example, an analytical column.

The extraction achieved with this microfluidic device can occur on-line or off-line. In general, "off-line" preferably means that the microfluidic device for extracting the biological sample may be physically near but unconnected to the process line. An individual uses the microfluidic device to extract a biological sample manually from the DBS card, then carries and introduces the extracted biological sample on the trapping tile to an analytical tile for sample analysis. "On-line" preferably means that the extraction and analysis microfluidic tiles are directly part of a process (or production) line to extract and analyze samples automatically from the process line in approximately real time without manual intervention. The chromatographic analysis can thus occur in parallel to the continued operation of the production/process line. FIG. 8 shows an embodiment of the DBS card 40 aligned to couple to a trapping tile 20 of the kind described in FIG. 2 and arranged in-line with an analytical tile 30 for "on-line" sample extraction and analysis.

Figure 9:
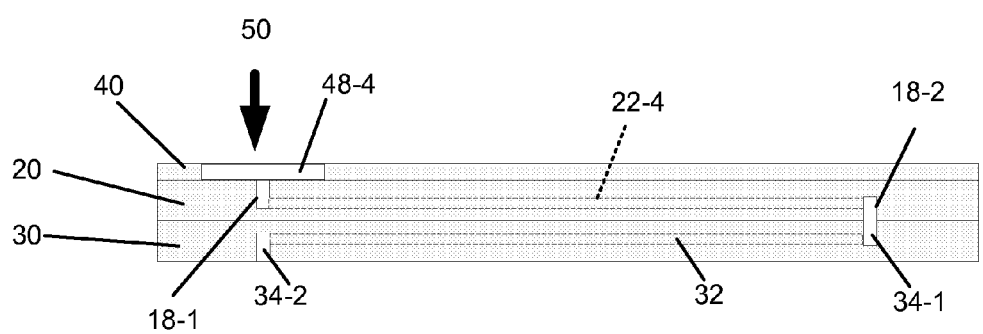
FIG. 9 is a cross-section, taken generally along the line CC in FIG. 8, of the DBS card abutting the first microfluidic substrate, and the first microfluidic substrate abutting the second microfluidic substrate.

FIG. 9 shows a cross-section (taken along a line like the line CC in FIG. 8) of the DBS card 40 abutting the trapping tile 20, and of the trapping tile 20 abutting the analytical tile 30. The cross-section passes through the blood spot 48-4, the ports 18-1, 18-2 of the trapping/enhancement column 22-4 in the trapping tile 20, and the ports 34-1, 34-2 of the analytical column 32 in the analytical tile 30. During extraction of a biological fluid sample on the dried blood spot 48-4, the biological sample is reconstituted by passing an extraction fluid or solvent in the direction of the dashed arrow 50 through or over the top of the dried sample spot 48-4.

The extracted reconstituted sample flows into the fluidic port 18-1 of the trapping tile 20, through the trapping/enhancement column 22-4, and out through the fluidic port 18-2. The extracted biological sample then flows into the fluidic port 34-1 of the analytical tile 30, through the analytical column 32, and out through the fluidic port 34-2. Elute from the analytical tile 30 passes to a detector or mass spectrometer system. Again, instead of using a complete DBS card 40, dried blood spots 48 can be individually punched out and coupled directly to the trapping tile 20 (at or near the fluidic port 18-1).

Figure 10:
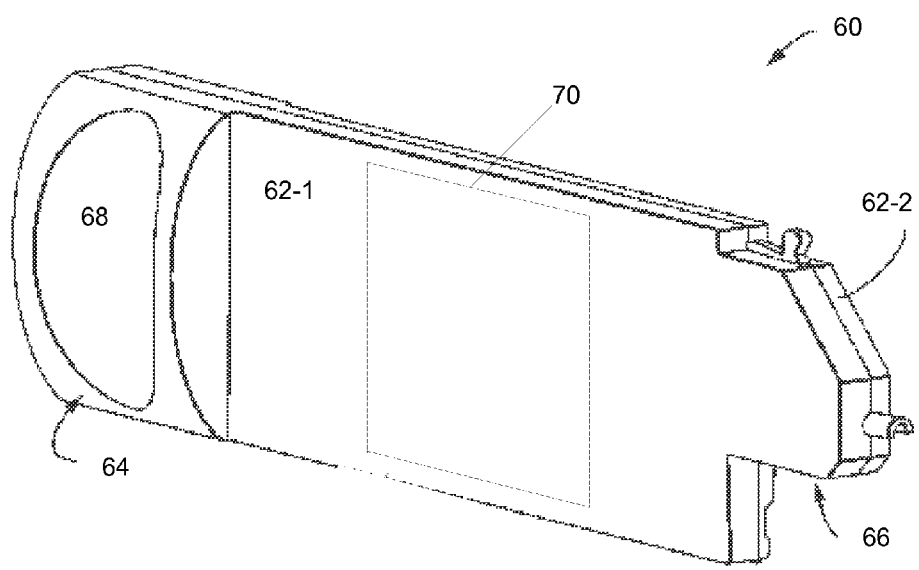
FIG. 10 is a diagram of an embodiment of a microfluidic cartridge assembly for holding multiple microfluidic substrates arranged for on-line processing.

FIG. 10 shows an embodiment of a microfluidic cartridge assembly 60 that can be used to interface the DBS card 40 and microfluidic substrates 20, 30, to a detector, mass spectrometer, or other chromatography apparatus. In brief, this embodiment of the microfluidic cartridge assembly 60 houses an emitter, multiple microfluidic substrates, a heater, and circuitry, and operates as an electromechanical interface for the delivery of voltages, electrical signals, and fluids (gas and liquid) to the various components housed within the microfluidic cartridge assembly 60.

This embodiment of microfluidic cartridge assembly 60 is made by joining two casing sections 62-1, 62-2, for example, by snapping the halves together, or using glue or mechanical fasteners, or any combination thereof. The microfluidic cartridge assembly 60 has a grip end 64 and an emitter end 66. A curved region 68 within the grip end 64 provides a finger hold by which a user can grasp the microfluidic cartridge assembly 60 when coupling it to the chromatography apparatus. One of the casing sections (here, e.g., section 62-1) can have an access panel 70 through which a technician can insert and remove a microfluidic device comprised of a DBS card 40 or an individually punched-out dried blood spot 48, and one or more microfluidic substrates 20, in a manner similar to how a battery is inserted and removed from a mobile phone. The biological sample substrates and microfluidic substrates of the microfluidic device are replaceable because the substrates with the biological sample and trapping/enhancement columns are separate from the microfluidic substrate with the analytical column. Accordingly, the analytical column remains in place with the removal of the DBS card 40, punched-out dried blot spot 48, or of a trapping/enhancement tile 20.

Figure 11:
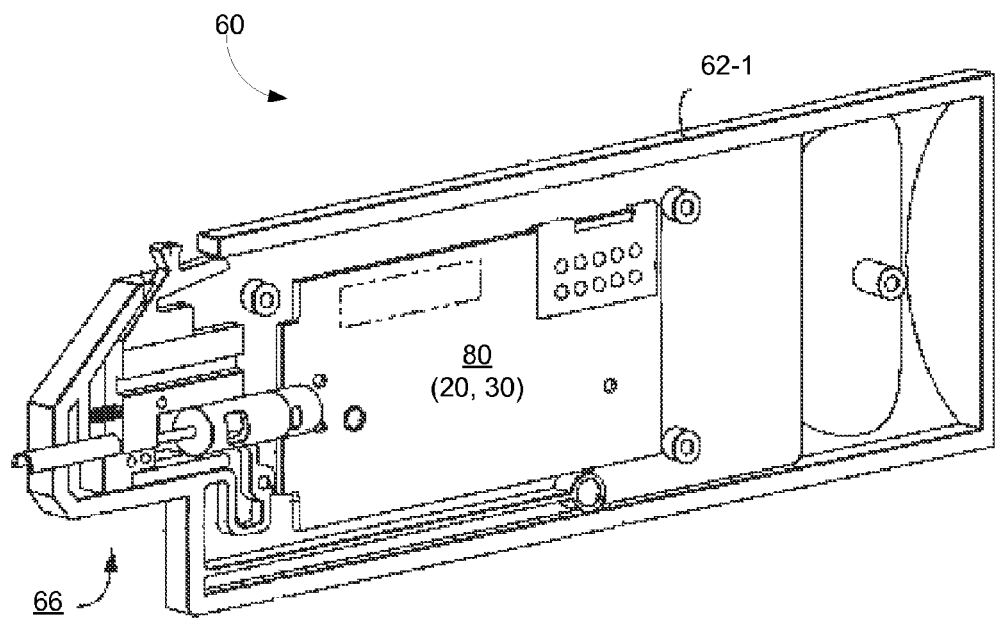
FIG. 11 is a diagram of the microfluidic cartridge assembly with a portion of its housing omitted to show the general location of the microfluidic substrates housed within.

FIG. 11 shows an embodiment of the microfluidic cartridge assembly 60 with the casing section 62-2 omitted to show various components housed within the assembly 60, including the stack 80 of microfluidic substrates 20, 30. The microfluidic cartridge assembly 60 can interface with an autosampler device (not shown) that is configured to index the multi-column trapping tile 20 and DBS card 40 automatically within the assembly 60. Manual indexing can also be implemented.

Various embodiments of microfluidic cartridge assemblies, such as the example described above, can be implemented with any suitable analytical apparatus. For example, some embodiments entail modified liquid-chromatography and/or mass-spectrometry apparatus, for example, an ACQUITY® or TRIZAIC® LC/MS system (available from Waters Corporation, Milford, Mass.)

Figure 12:
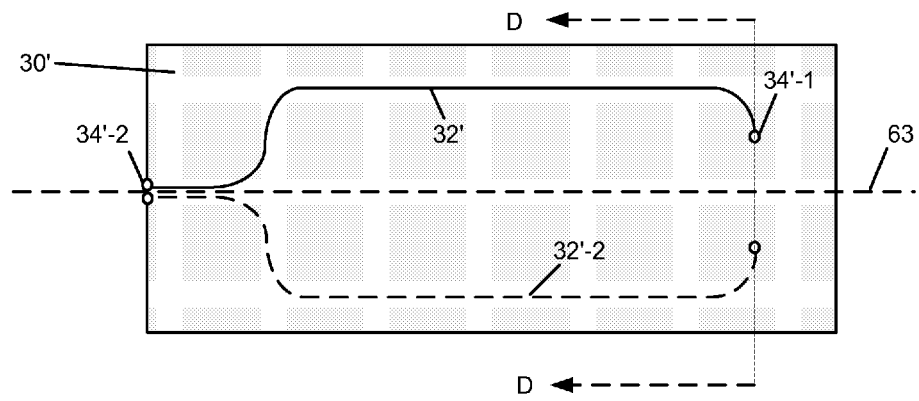
FIG. 12 is a diagram of another embodiment of a microfluidic substrate that can be interfaced to a DBS card, a dried blood spot, and other microfluidic substrates within the microfluidic cartridge assembly.

FIG. 12 shows another embodiment of an analytical tile 30' that can be used within the microfluidic cartridge assembly 60 in conjunction with other substrates, for example, a DBS card 40 and a trapping/enhancement tile 20. The analytical tile 30' includes an analytical column 32' with an ingress fluidic port 34'-1 and an egress fluidic port 34'-2. The ingress port 34'-1 is adapted for fluidic communication with an egress fluidic port 18-2 of the separate, abutting trapping/enhancement tile 20. The ingress fluidic port 34'-1 is a through-hole port that opens on both sides of the microfluidic substrate 30', and can be coupled to a fluidic nozzle and tubing, to allow head-of-the-column dilution of an incoming sample (as may be desired for a reversed phase chromatography process). For instance, to enable retention on a reverse phase column, dilution with water may be necessary for an extracted biological sample with a high amount of organic solvent. Through the fluidic nozzle and tubing, a dilution pump can pump a solvent (e.g., water) into the ingress fluidic port 34'-1. Because the fluidic port 34'-1 is at the head of the analytical column 32', the solvent operates to dilute the biological sample before the biological sample enters the analytical column 32'.

The egress fluidic port 34'-2 opens at the edge of the analytical tile 30'. This edge faces the emitter end 66 of the microfluidic cartridge assembly 60 of FIG. 11. The analytical tile 30' can optionally include another (mirror image) analytical column 32' to allow the analytical tile 30' to be installed in the cartridge assembly 60 in one of two orientations (i.e., the analytical tile 30' is symmetric about a horizontal axis 63).

Figure 13:
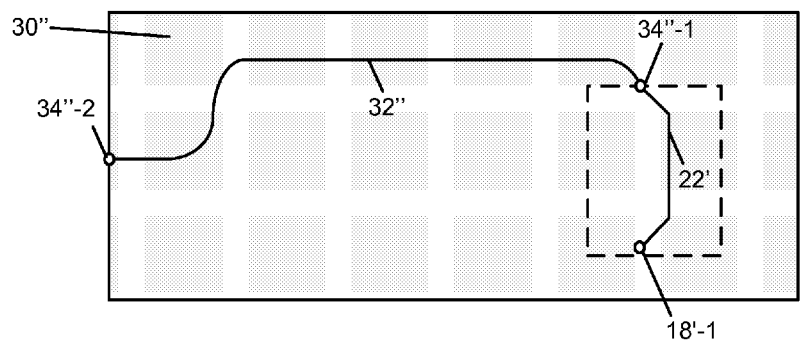
FIG. 13 is a diagram of another embodiment of a microfluidic substrate with an analytical column that can be interfaced to a DBS card or a dried blood spot within the microfluidic cartridge assembly.

FIG. 13 shows another embodiment of an analytical tile 30" that can be used within the microfluidic cartridge assembly 60 in conjunction with a DBS card 40 or an individual dried blood spot 48. The analytical tile 30" includes a trapping/enhancement column 22' integrated on the same substrate with an analytical column 32".

The analytical column 32" has an ingress fluidic port 34"-1 and an egress fluidic port 34"-2. The ingress fluidic port 34"-1 is a port that opens on one (either) or both sides of the microfluidic substrate 30", and can be coupled to a fluidic nozzle and tube, to allow head-of the-column dilution of a sample (e.g., for a reversed phase chromatography process) arriving from the trapping/enhancement column 22'. A dilution pump can pump a solvent into the ingress fluidic port 34"-1, which operates to dilute the biological sample before the biological sample enters the analytical column 32". The diluted biological sample passes through the analytical column 32", which separates the biological sample into is constituent components. The components exit the analytical column 32", for example, in the form of electrospray delivered to a LC detector or mass spectrometer system.

The integrated trapping/enhancement column 22' includes an ingress fluidic port 18'-1, which can be coupled to a dried blood spot for on-line processing with the analytical tile 30". In one embodiment, the trapping/enhancement column 22' can be configured for solid-phase extraction (SPE) to clean the biological sample in preparation for analysis as is generally known in the art. The trapping/enhancement column 22' merges into the analytical column 32" at the ingress fluidic port 34"-1.

Figure 14:
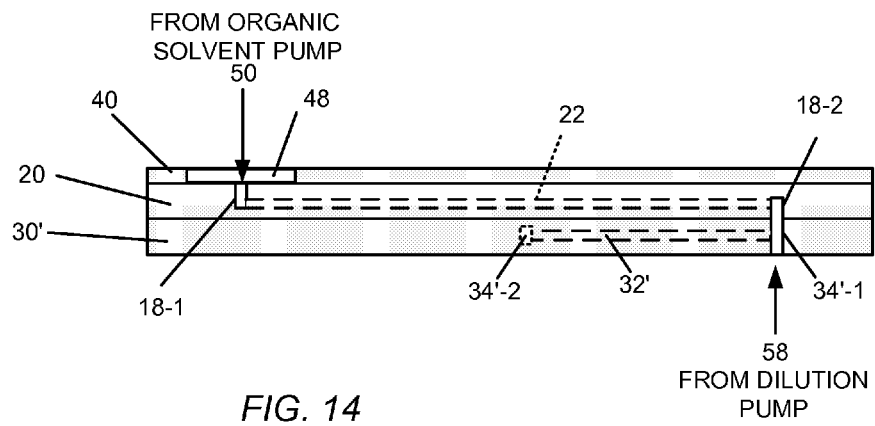
FIG. 14 is a cross-section, taken generally along the line DD in FIG. 12, of the DBS card of FIG. 8 abutting a microfluidic substrate (i.e., trapping/enhancement tile) of FIG. 8, and of a microfluidic substrate abutting the microfluidic substrate (i.e., analytical tile) of FIG. 12.

FIG. 14 shows a cross-section (taken along a line like the line DD in FIG. 12) of the DBS card 40 (FIG. 8) abutting the trapping/enhancement tile 20 (FIG. 2), and of the trapping/enhancement tile 20 abutting the analytical tile 30' of FIG. 12. The cross-section passes through the blood spot 48-4, through the fluidic ports 18-1, 18-2 of the fluidic channel 22 in the trapping/enhancement tile 20, and through the ports 34'-1, 34'-2 of the fluidic channel 32' in the analytical tile 30'.

During extraction of a biological fluid sample on the dried blood spot 48-4, the dried biological sample is reconstituted by passing an extraction fluid or solvent in the direction of the dashed arrow 50 through the dried sample spot 48-4. Again, instead of using a complete DBS card 40, dried blood spots 48 can be individually punched out and coupled directly to the trapping/enhancement tile 20 (at or near the fluidic port 18-1).

The extracted reconstituted sample flows through or over the top of the dried sample spot 48-4 and into the fluidic port 18-1 of the trapping/enhancement tile 20, through the trapping/enhancement column 22-4, and out through the fluidic port 18-2. The extracted biological sample then flows into the fluidic port 34'-1 of the analytical tile 30'.

The fluidic port 34'-1 is at the head of the analytical column 32', and, in one embodiment, is coupled to a dilution pump that pumps a solvent (e.g., water) into the fluidic port 34'-1 in the direction of arrow 58. The solvent operates to dilute the biological sample leaving the trapping/enhancement column 22 before the sample enters the analytical column 32'. The diluted biological sample passes through the analytical column 32', which separates the sample into its constituent components. The components exit the analytical column 32' in the form of an electrospray, for example, directed at a detector or mass spectrometer system.

Figure 15:
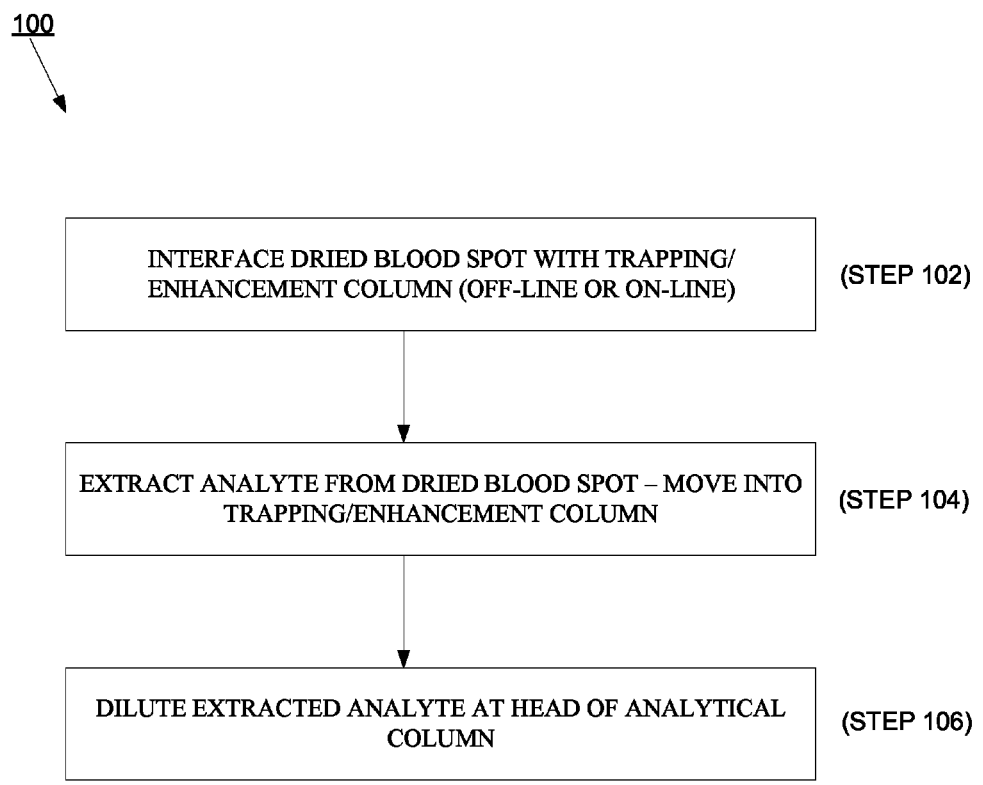
FIG. 15 is a flow diagram of an embodiment of a process for performing a chromatographic analysis of a biological sample deposited on a dried blood spot.

FIG. 15 shows an embodiment of a process 100 for performing a chromatographic analysis of a dried blood spot (e.g., 48-4). At step 102, a dried blood spot (e.g., punched out or part of a DBS card) is interfaced to a microfluidic substrate with a trapping/enhancement column A solvent flows (step 104) over or through the dried blood spot to extract the analyte. The extracted analyte flows into the trapping/enhancement column. The extraction of the analyte can occur off-line, in which instance, the trapping/enhancement tile holding the extracted analyte is carried to and placed in-line with a microfluidic substrate having an analytical column. The extracted analyte is diluted at the head of the analytical column. The analytical column separates the constituent components of the diluted analyte. An electrospray emitter may be fluidically coupled to the egress end of the analytical column for delivering the separated constituents to an LC instrument as an electrospray.

Reference in the specification to "one embodiment" or "an embodiment" means that a particular, feature, structure or characteristic described in connection with the embodiment is included in at least one embodiment of the teaching. References to a particular embodiment within the specification do not all necessarily refer to the same embodiment.

While the invention has been shown and described with reference to specific preferred embodiments, it should be understood by those skilled in the art that various changes in form and detail may be made therein without departing from the spirit and scope of the invention as defined by the following claims.

What is claimed is:

1. A chromatography apparatus comprising:
   a first microfluidic substrate having a first fluidic channel comprising an analytical chromatographic column and a first fluidic port on one side of the first microfluidic substrate, the first fluidic port opening at a head end of the analytical chromatographic column; and
   a second microfluidic substrate having a second fluidic channel comprising a sample-preparation column, a second fluidic port on a first side of the second microfluidic substrate and opening into an end of the sample-preparation column, the sample-preparation column terminating at the head end of the analytical column, and a third fluidic port on a second side of the second microfluidic substrate;
   a dried blood spot (DBS) collection device holding one or more dried biological samples, the DBS collection device being directly coupled to the second microfluidic substrate whereby one of the biological samples is placed into fluidic communication with the second fluidic channel of the microfluidic substrate such that the second fluidic port of the second microfluidic substrate receives an extraction of that biological sample and passes the extracted biological sample into the sample-preparation column;

wherein the second side of the second microfluidic substrate is coupled to the first microfluidic substrate such that the third fluidic port of the second microfluidic substrate is in fluidic communication with the first fluidic port of the first microfluidic substrate and produces a fluidic path comprised of the sample-preparation column and the analytical chromatographic column; and a diluent source fluidically coupled to the first fluidic port, the diluent source supplying a solvent to the head end of the analytical column to dilute the extracted biological sample before the biological sample flows into the analytical chromatographic column.

2. The chromatography apparatus of claim 1, wherein the sample-preparation column comprises a solid-phase extraction (SPE) device.

3. The chromatography apparatus of claim 1, wherein the DBS collection device coupled directly onto the second microfluidic substrate has a different dried biological sample in fluidic communication with a different fluidic channel of the second microfluidic substrate, and the DBS collection device and the second microfluidic substrate are movably coupled.

4. The chromatography apparatus of claim 3, further comprising an autosampler device mechanically coupled to the DBS collection device and to the second microfluidic substrate for indexing a different one of the sample-preparation columns of the microfluidic substrate into alignment with a sample-preparation column.

5. The chromatography apparatus of claim 1, further comprising a pump fluidically coupled to one side of the DBS collection device to pump solvent to the dried biological sample in order to extract an analyte therefrom.

6. The chromatography apparatus of claim 5, wherein the pumped solvent is a supercritical fluid.

7. The chromatography apparatus of claim 5, wherein the pumped solvent is an organic solvent.

8. The chromatography apparatus of claim 5, wherein the pumped solvent is delivered to the one side of the DBS collection device such that the pumped solvent passes through the biological sample in order to extract the analyte.

9. The chromatography apparatus of claim 5, wherein the pumped solvent is delivered to the one side of the DBS collection device such that the pumped solvent flows atop the biological sample in order to extract the analyte.

10. The chromatography apparatus of claim 1, wherein the analytical chromatographic column has a 300 µm inner diameter.

11. The chromatography apparatus of claim 1, wherein the DBS collection device is a DBS card containing a plurality of dried biological samples.

12. The chromatography apparatus of claim 1, wherein the extraction and analysis of the biological sample occurs on-line.

13. The chromatography apparatus of claim 1, further comprising a microfluidic cartridge assembly housing the microfluidic substrate and the DBS collection device.

14. A method of separating a biological sample into constituent components, the method comprising:

coupling a dried blood spot (DBS) collection device, holding at least one dried biological sample, directly to a first fluidic channel on a first microfluidic substrate, the first fluidic channel configured as a sample-preparation column;

extracting an analyte from the dried biological sample and passing the extracted biological sample into the first fluidic channel comprising the sample-preparation column of the microfluidic substrate;

coupling the first microfluidic substrate to a second microfluidic substrate such that a first fluidic port of the first microfluidic substrate is in fluidic communication with a second fluidic port of the second microfluidic substrate and produces a fluidic path comprised of the sample-preparation column and the analytical chromatographic column;

passing the extracted biological sample that elutes from the sample-preparation column into a second fluidic channel on the second microfluidic substrate, the second fluidic channel comprising an analytical chromatographic column diluting the extracted biological sample in the second fluidic channel before the extracted biological sample reaches the analytical chromatographic column; and separating, by the analytical chromatographic column, the diluted biological sample into constituent components.

15. The method of claim 14, wherein the sample-preparation column comprises a solid-phase extraction (SPE) device.

16. The method of claim 14, wherein the DBS collection device has a different dried biological sample in fluidic communication with a different fluidic channel of the first microfluidic substrate, and the DBS collection device and the first microfluidic substrate are movably coupled, and further comprising indexing a different one of the sample-preparation columns of the first microfluidic substrate into fluidic communication with a dried biological sample on the DBS collection device.

17. The method of claim 14, further comprising pumping solvent to the dried biological sample in order to extract an analyte therefrom.

18. The method of claim 17, wherein the pumped solvent is a supercritical fluid.

19. The method of claim 17, wherein the pumped solvent is an organic solvent.

20. The method of claim 19, further comprising passing the pumped solvent through the dried biological sample in order to extract the analyte.

21. The method of claim 19, further comprising passing the pumped solvent over atop the dried biological sample in order to extract the analyte.

22. The method of claim 14, wherein the analytical chromatographic column has a 300 µm inner diameter.

23. The method of claim 14, wherein the DBS collection device is a DBS card containing a plurality of dried biological samples.

24. The method of claim 14, wherein the extracting of the biological sample from the DBS collection device and separating the constituent components of the extracted biological sample occurs on-line.

* * * * *